US010429307B2

(12) United States Patent
Jagiella et al.

(10) Patent No.: US 10,429,307 B2
(45) Date of Patent: Oct. 1, 2019

(54) SPECTROMETRIC MEASURING DEVICE

(71) Applicant: Endress+Hauser Conducta GmbH+Co. KG, Gerlingen (DE)

(72) Inventors: Manfred Jagiella, Notzingen (DE); Michael Weiss, Lörrach (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 20 days.

(21) Appl. No.: 15/655,992

(22) Filed: Jul. 21, 2017

(65) Prior Publication Data

US 2018/0031482 A1 Feb. 1, 2018

(51) Int. Cl.
*G01N 21/65* (2006.01)
*G01J 3/02* (2006.01)
(Continued)

(52) U.S. Cl.
CPC ............ *G01N 21/65* (2013.01); *G01J 3/0205* (2013.01); *G01J 3/0264* (2013.01); *G01J 3/0291* (2013.01);
(Continued)

(58) Field of Classification Search
CPC .......... G01J 3/44; G01J 3/0291; G01J 3/0205; G01J 3/0264; G01J 3/108; G01J 3/4412;
(Continued)

(56) References Cited

U.S. PATENT DOCUMENTS 5,862,273 A 1/1999 Pellietier
6,141,095 A * 10/2000 Allen ................... G01J 3/28
356/301
(Continued)

FOREIGN PATENT DOCUMENTS

WO 2006081380 A2 8/2006

OTHER PUBLICATIONS

Search Report for German Patent Application No. 10 2016 113 884.3, German Patent Office, dated Jun. 9, 2017, 3 pp.
(Continued)

Primary Examiner — Michael C Bryant
(74) Attorney, Agent, or Firm — Christopher R. Powers; PatServe

(57) ABSTRACT

The present disclosure relates to a spectrometric measuring device for a process measuring point including a housing, a radiation source arranged in the housing, a coupling and decoupling optical system to direct radiation from the radiation source into a measuring region and to couple measuring radiation from the measuring region into the housing, a spectrograph arranged in the housing and aligned such that the measuring radiation is detected by the spectrograph with a detector, an electronic device arranged in the housing and connected to the detector and configured to detect a spectrum from the spectrograph and to process it to determine a concentration of an analyte in the measuring medium or a value derived therefrom, and a connection connected to the housing for connecting the housing to a process container, wherein the measuring region is located within a volume of the process container, said volume containing the measuring medium.

24 Claims, 6 Drawing Sheets

(51) Int. Cl.
*G01J 3/10* (2006.01)
*G01J 3/44* (2006.01)
*G01N 21/35* (2014.01)
*G01N 33/49* (2006.01)

(52) U.S. Cl.
CPC ............. *G01J 3/108* (2013.01); *G01J 3/4412* (2013.01); *G01N 21/35* (2013.01); *G01N 33/49* (2013.01); *G01N 2201/022* (2013.01)

(58) Field of Classification Search
CPC .. G02F 1/35; G01N 21/55; G02B 1/04; A61B 5/0082; A61B 5/443
See application file for complete search history.

(56) References Cited

U.S. PATENT DOCUMENTS

| | | | | |
|---|---|---|---|---|
| 8,699,020 | B1* | 4/2014 | Zhou | G01J 3/0264 356/301 |
| 2001/0043329 | A1* | 11/2001 | Hustert | G01J 3/46 356/402 |
| 2005/0269499 | A1* | 12/2005 | Jones | B08B 7/028 250/269.1 |
| 2008/0174777 | A1* | 7/2008 | Carron | G01J 3/02 356/328 |
| 2009/0285526 | A1* | 11/2009 | Mikkelsen | G01N 21/0317 385/31 |
| 2012/0029326 | A1* | 2/2012 | Kawamura | A61B 5/14532 600/310 |
| 2012/0062881 | A1* | 3/2012 | Sakagami | G01N 21/658 356/301 |
| 2012/0062882 | A1 | 3/2012 | Sakagami et al. | |
| 2012/0062884 | A1* | 3/2012 | Sakagami | G01J 3/0224 356/301 |
| 2012/0265038 | A1 | 10/2012 | Kawamura et al. | |
| 2012/0274935 | A1* | 11/2012 | Yamada | G01N 21/05 356/301 |
| 2014/0296665 | A1 | 10/2014 | Yamada | |
| 2015/0139856 | A1 | 5/2015 | Yamada et al. | |
| 2015/0164393 | A1 | 6/2015 | Kawamura et al. | |

OTHER PUBLICATIONS

Explosion-Proof Enclosures for Use in Class I Hazardous Locations, CSA Standard C22.2 No. 30-M1986, 1999, 54 pp.
Approval Standard for Explosionproof Electrical Equipment General Requirements Class No. 3615, FM Approvals LLC, Aug. 2006, 33 pp.
Explosive atmospheres—Part 1: Equipment protection by flameproof enclosures "d", International Standard, IEC 60079-1, International Electrotechnical Commission, ed. 7.0 Jun. 2014, 193 pp.

* cited by examiner

SPECTROMETRIC MEASURING DEVICE

CROSS-REFERENCE TO RELATED APPLICATIONS

The present application is related to and claims the priority benefit of German Patent Application Nos. 10 2016 113 884.3, filed on Jul. 27, 2016 and 10 2016 123 349.8, filed Dec. 2, 2016, the entire contents of which are incorporated herein by reference.

TECHNICAL FIELD

The present disclosure relates to a spectrometric measuring device particularly a Raman spectrometer for a process measuring point.

BACKGROUND

In production processes, spectrometric measurements can be performed in gases, liquids, solids, and multiphase mixtures in order to obtain knowledge about the production process or about a substance formed as a product of the process, for example, its quantity and quality. From spectrometric measurements, values of measurands correlating to the concentration of educts and/or additives of the process can also be obtained. For example, in a biochemical production process, concentrations of nutrients and/or concentrations of metabolites of the microorganisms used in the production process and/or the concentration of the product produced in the process in a process medium can be monitored, and the process sequence can be controlled and/or regulated based upon the measured data obtained. The process medium is generally contained in a process container, such as a reactor, a fermenter, or in a duct.

A spectrometric method very well-suited for analyzing and monitoring gaseous, solid, and liquid process media is Raman spectroscopy. It is based upon the inelastic scattering, called the Raman effect, of electromagnetic radiation by atoms or molecules. The largest portion of the radiation radiated into a measuring medium is elastically scattered by the molecules of the measuring medium as so-called Rayleigh scattering. This portion of the scattered radiation has the same wavelength as the excitation radiation. In the inelastic scattering by molecules of the sample, an energy transfer takes place, wherein a molecule interacting with the excitation radiation can transition via a virtual state into an energetically higher state (Stokes scattering) or into an energetically lower state (anti-Stokes scattering). In the first case, energy is consumed, so that the scattered radiation has a lower energy than the excitation radiation. In the other case, energy is released, so that the scattered radiation has a higher energy than the excitation radiation. A Raman spectrum is an illustration of the intensity of the inelastically scattered radiation as a function of its frequency difference from the excitation radiation (generally specified in wavenumbers, cm-1). The Raman spectroscopy is a vibrational spectroscopy, i.e., the energy transfers detected using Raman spectroscopy correspond to characteristic vibration energy levels of the molecules or their functional groups. Thus, based upon certain peaks or bands in the Raman spectrum, the presence of certain molecules in the sample and, based upon the intensity of the respective peaks or bands, their concentration, can be determined.

Especially advantageous in Raman spectroscopy in connection with process media containing water, for instance, biological systems or biotechnological processes, is the fact that water is a very weak Raman scatterer, so that Raman signals of molecules dissolved in water can be seen easily in the Raman spectrum of the solution. In addition, Raman spectroscopy does not require any additional preparation of the sample and can provide measured values in a short time. This method is thus especially attractive for process analysis and process control.

In the prior art, it is customary to take samples of a process medium from the process container and to examine them in the laboratory by means of a spectrometer in order to determine values of the respective measurands to be determined from the spectral data obtained. The spectra detected using the spectrometer can be analyzed by means of a data processing unit, e.g., a conventional computer. Problematic in this case is the sampling, since it results in a significant time delay between the taking of the sample from the process container and the availability of the final measured value. Moreover, the taking of samples from processes to be kept sterile, e.g., in food technology and in processes of the pharmaceutical industry and/or of biotechnology, is associated with a high investment in equipment and personnel in order to take the samples properly and without contaminating the process. Depending upon the type of process, a health hazard can also exist during the sampling, if an undesired contact of the sample or the process medium with the environment of the process container occurs.

From U.S. Pat. No. 5,862,273 is known a Raman spectrometer with a probe, which can be integrated as a spectrometric interface as an inline probe into the process container. The probe is connected to additional components of the spectrometer, such as a laser radiation source and a spectrograph via optical waveguides in the form of optical fibers. Disadvantageous in such a spectrometric measuring device with a probe connected to the actual spectrometer, and possibly an additional evaluation unit via optical waveguides, is the fact that such a wave guide connection cannot be realized over any arbitrary distance. In addition, the optical properties of the fibers can influence the measurement or must be suppressed by suitable means, e.g., filters. This increases the equipment investment.

From WO 2006/081380 A2 is known a compact Raman spectrometer, which includes a laser light source, a low-resolution dispersion element, and a detection array, which are accommodated in a single housing. A sample to be examined is introduced into the compact spectrometer on an object holder. This compact spectrometer indeed does not require any wave guides extending outside the housing; on the other hand, it is not suitable for being connected to a process especially, an industrial process.

SUMMARY

It is therefore the aim of the present disclosure to specify a spectrometric measuring device that overcomes the disadvantages of the measuring devices known from the prior art. The measuring device is to be suitable for the application in process analysis and also for the integration in a control and/or regulation of processes.

This aim is achieved by the spectrometric measuring device according to claim 1 and the process measuring point according to claim 16. Further embodiments are listed in the dependent claims.

The spectrometric measuring device according to the present disclosure for a process point, which can, especially, be a Raman spectrometer, includes: a housing; a radiation source arranged in the housing; a coupling and decoupling optical system, which is designed to decouple radiation of the radiation source from the housing and radiate it into a measuring region arranged outside the housing, and to couple measuring radiation from the measuring region into the housing; a spectrograph, which is arranged in the housing and aligned in relation to the coupling and decoupling optical system such that radiation coupled into the housing from the measuring region via the coupling and decoupling optical system is detected by the spectrograph, and wherein the spectrograph is configured to disperse the radiation detected into a spectrum and to register the generated spectrum by means of a detector; an electronic device component, which is arranged in the housing and which is connected to the detector and configured to detect the spectrum registered by means of the detector and to process it to determine, based upon the spectrum, a measurand correlated to the concentration of at least one analyte in the measuring medium; and a connection means, which is connected to the housing especially, firmly connected to the housing for connecting the housing to a process container, which contains a measuring medium, wherein the measuring region is located within a volume area of the process container, said volume area containing the measuring medium.

By arranging the radiation source, the coupling and decoupling optical system, the spectrograph, and the electronic device component in a housing of the measuring device, especially in a single housing of the measuring device, the measuring device is designed very compactly and can do without a process probe that must be connected by means of a wave guide to a spectrometer possibly arranged at a distance from the process. By means of the connection means connected to the housing, the measuring device can be affixed to a connection of a process container. The housing can be designed to be sealed, for example, hermetically sealed and can thus shield the optical system and electronic component of the spectrometric measuring device from negative influences of the process, aggressive chemicals, or an environment at risk of explosion. The measuring device can thus be used universally in processes with various requirements.

In one embodiment, the spectrometric measuring device can further comprise a power supply unit arranged in the housing, which power supply unit supplies power to the radiation source and the electronic device component.

The connection means of the device can comprise a process connection, which can be affixed to a complementary connection of a process container, for example, of a pipe carrying the measuring medium or of a reaction container containing the process medium, e.g., a fermenter.

In an alternative embodiment, the connection means can comprise a flow-through cell or a spool piece, which has connections, such as flanges on two opposite ends and which can be installed in a process container, for example, in a pipe carrying the measuring medium.

The electronic device component can comprise at least one microprocessor and one non-volatile memory, in which a computer program is stored which provides functionalities of the spectrometric measuring device and can be executed by the microprocessor, wherein the computer program serves to control the spectrometric measuring device, especially, the radiation source, controllable parts of the coupling and decoupling optical system, the detector, and/or the power supply unit of the measuring device and to register and process the spectrum.

The radiation source can comprise a substantially monochromatic radiation source of high intensity, for example, a laser wherein at least a portion of the measuring radiation coupled into the housing from the measuring region is generated by Raman scattering of the radiation of the radiation source radiated into the measuring region.

The spectrograph can comprise an optical filter, which serves to remove the portion of the measuring radiation generated by the elastic Rayleigh scattering. The spectrograph and the electronic device component can register and process a Raman spectrum generated by Stokes scattering and/or anti-Stokes scattering.

The coupling and decoupling optical system can comprise at least one window that is arranged in a wall of the housing and is transparent to the radiation of the radiation source and to the measuring radiation. In one embodiment, the coupling and decoupling optical system can have at least one coupling wave guide connecting the radiation source and the window, and one decoupling wave guide connecting the window and the spectrograph. The coupling and decoupling can, however, also take place without a wave guide, using traditional optical elements, such as lenses and mirrors, to form and steer the beams.

In an advantageous embodiment, the measuring device can further have an ultrasound source connected to the window or arranged near the window, for example, on the outside of the housing, and/or connected to the connection means for cleaning the window.

In an advantageous embodiment, the housing is explosion-proof, e.g., in accordance with the protection class Ex-d. At the same time or alternatively, the housing can be splash-proof.

The electronic device component can have at least one interface for wireless or wired communication with a control unit arranged outside the housing. The control unit can be designed to process the signals output by the electronic device component. Preferably, the control unit serves to control the process, in that a process medium as measuring medium is monitored by the spectrometric measuring device.

If an interface for wireless communication is provided, it can be designed for communication in accordance with a Bluetooth standard especially, Bluetooth 4.0 or Bluetooth Low Energy. This allows for communication with a Bluetooth-enabled, portable operator unit, such as a tablet PC or a smartphone which is provided with operating software for the measuring device, which operating software is especially designed as mobile application software (app or mobile app).

The electronic device component and/or the control unit and/or the operator unit can have a processor and a non-volatile memory, wherein, in the non-volatile memory, a computer program is stored, which can be executed by the processor and which serves to determine from the registered spectrum a concentration of at least one analyte, including a plurality of analytes in the measuring medium or a measurand derived therefrom. The analyte can, for example, be glucose.

The coupling and decoupling optical system can comprise at least a first wave guide and can transmit radiation from the radiation source to the measuring medium, and/or wherein a second wave guide transmits measuring radiation from the measuring medium to the spectrograph.

The radiation source can radiate radiation of a wavelength in the infrared range.

The spectrometric measuring device can comprise a mirror device, which deflects incoming measuring radiation toward the detector.

In doing so, the mirror device can comprise at least a first mirror and a second mirror, and the mirrors can respectively be tilted independently of each other at least between a first position and a second position, wherein the mirrors, when in the first position, deflect the measuring radiation toward the detector.

The spectrometric measuring device can comprise a dispersion element, which splits measuring light at least into measuring light of a first wavelength and a second wavelength, and wherein the first mirror of the aforementioned mirror device then deflects measuring light of the first wavelength toward the detector, and wherein the second mirror of the aforementioned mirror device deflects measuring light of the second wavelength toward the detector.

In one embodiment, the detector is designed as a single-point detector, i.e., not as a matrix or array.

The present disclosure also relates to a process measuring point comprising at least one spectrometric measuring device according to one of the preceding claims and one process container connected to the housing of the spectrometric measuring device via the connection means. The process container can, for example, be a pipe carrying the measuring medium or a reactor or fermenter containing the measuring medium.

The connection means can comprise an immersion changeover device integrated into the wall of the process container, which device is designed to move at least a process-side portion of the housing, which comprises a window serving to couple and decouple radiation into the measuring region located in the process container, between a service position retracted into a service chamber of the device and a measuring position extended into the process container.

The process measuring point can further comprise an operator unit arranged outside the housing and connected to the electronic device component in a wireless or wired manner for communication and/or a control unit arranged outside the housing and connected to the electronic device component in a wireless or wired manner for communication. The operator unit and/or the control unit can, for example, comprise a measuring transducer. The operator unit can, for example, be a portable device, such as a smartphone or a tablet PC. The operator unit can also be a measuring transducer or an industrial PC connected to the electronic device component via a signal line, via which, for example, data and possibly also power can be transmitted. The operator unit, in turn, can be connected to a control station via a fieldbus. The electronic device component can, alternatively, also be connected directly via a fieldbus in a wireless or wired manner to a control unit, for example, a programmable logic controller.

BRIEF DESCRIPTION OF THE DRAWINGS

In the following, the present disclosure is described in more detail with reference to the exemplary embodiments shown in the figures. The figures show.

DETAILED DESCRIPTION

Figure 1:
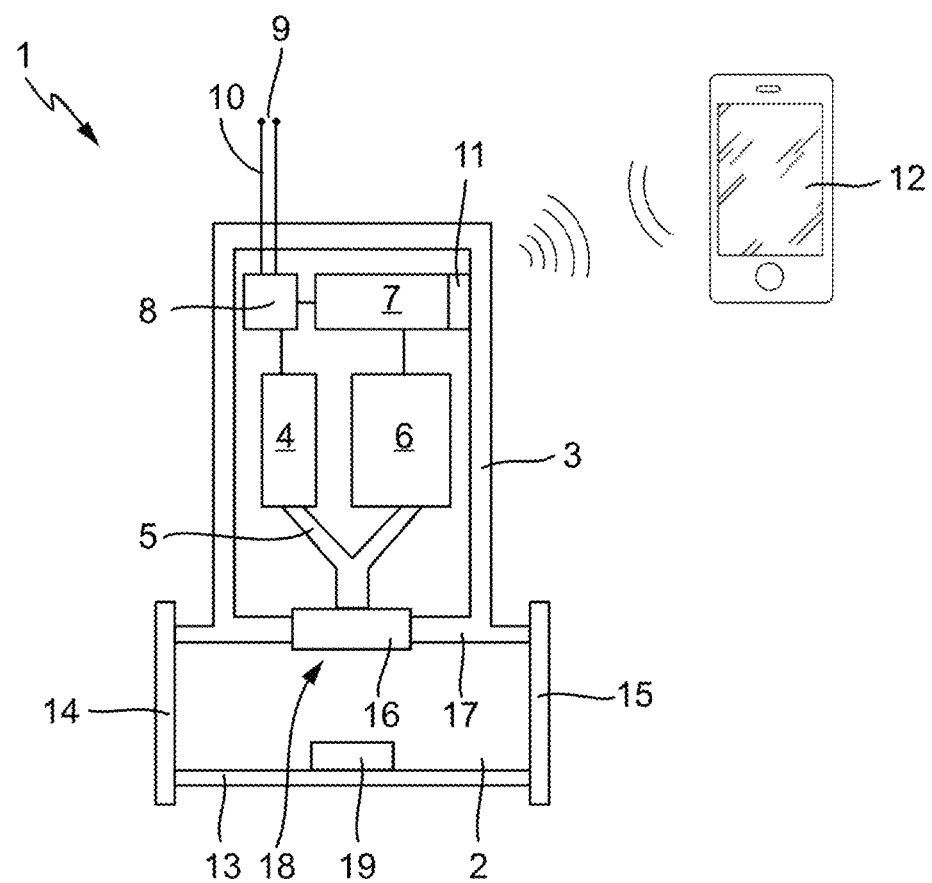
FIG. 1 shows an embodiment of a spectrometric measuring device according to the present disclosure.

FIG. 1 schematically illustrates a spectrometric measuring device 1, which serves to detect Raman spectra of a solid, liquid, or gaseous measuring medium 2. The measuring device 1 comprises a housing 3, in which a radiation source 4, a coupling and decoupling optical system 5, a spectrograph 6, an electronic device component 7, and a power supply unit 8 are arranged. The power supply unit 8 is electrically conductively connected via a power and/or signal cable 10 to a voltage source 9 arranged outside the housing 3. The measuring device 1 can be supplied with power via the signal cable 10, wherein the signal cable 10 at the same time serves to connect the measuring device 1 to a higher-level control unit (not shown) and allows for bi-directional communication between the control unit and the measuring device 1. The electronic device component 7 has a radio interface 11, which is designed to communicate data stored and generated in the electronic device component 7 to an operator unit 12 in accordance with the Bluetooth standard, for example, Bluetooth 4.0 or higher. The radio interface 11 is also designed to receive data from the operator unit 12 via radio in accordance with the Bluetooth standard and to output them to the electronic device component 7 for further processing. The radio interface 11 can alternatively or additionally be designed to transmit data by means of WLAN and/or Ethernet.

To the housing 3 is connected a flow-through cell 13, which has connections 14 and 15, which can be connected to a process container containing the measuring medium. In the present example, the flow-through cell 13 can be installed in a duct carrying the measuring medium 2 in a processing system or in a bypass of such a duct. In the flow-through cell 13, additional sensors, such as flow rate sensors, temperature sensors, electrochemical analysis sensors, such as oxygen, pH, or conductivity sensors, or pressure sensors can optionally be installed (not shown here).

In the present example, the spectrometric measuring device 1 is designed to detect Raman spectra. Of course, the radiation source, spectrograph, coupling and decoupling optical system, and the electronic device component can additionally or alternatively also be designed to detect additional spectra, such as absorption or fluorescence spectra in different wavelength ranges. The measuring device can have several radiation sources, which respectively emit radiation of different wavelength ranges.

In the present example, the radiation source 4 is a laser, which emits substantially monochromatic radiation of a wavelength in the wavelength range between 500 and 1000 nm.

The coupling and decoupling optical system 5 comprises, in the example shown here, a wave guide, which can be composed of a plurality of optical fibers, and a window 16. On the one hand, the wave guide connects the radiation source 4 to the window 16 and, on the other hand, the window 16 to the spectrograph 6. The window 16 is integrated into a housing wall 17 of the housing 3, which wall at the same time forms a wall of the flow-through cell 13. The coupling and decoupling optical system 5 is designed to decouple radiation emitted by the radiation source 4 from the housing 3 and to focus it into a measuring region 18 located in the flow-through cell 13 outside the housing 3. To this end, the coupling and decoupling optical system can have additional optical elements such as lenses (not shown here). Likewise, the coupling and decoupling optical system is designed to couple the radiation (also called measuring radiation herein) scattered by molecules of a measuring medium present in the measuring region 18 back into the housing 3 and to deliver it to the spectrograph 6 via the wave guides.

As explained above, the measuring radiation comprises a high proportion of elastically-scattered Rayleigh radiation, as well as a portion of longer-wave radiation (Stokes radiation) generated by inelastic scattering and a portion of shorter-wave radiation (anti-Stokes radiation) generated by inelastic scattering. The spectrograph 6 comprises an optical element, such as a mirror, a filter, or a lattice, which is configured to filter out the Rayleigh radiation portion from the measuring radiation. In addition, the spectrograph 6 comprises a dispersive element for the spectral isolation of individual wavelengths, for example, in the wavelength range of the Stokes radiation of the measuring radiation freed of the Rayleigh radiation portion, and a detector, which detects their intensity as a function of the wavelength and registers it in the form of a spectrum. The detector can, for example, comprise a photodiode cell or a photodiode array, a CCD array, or a CCD camera. In order to transmit data, the detector is connected to the electronic device component 7 so that the registered spectrum can be output to the electronic device component 7 for further processing.

In order to control the measuring device 1, the electronic device component 7 is also connected to the radiation source 4 and the spectrograph 6, as well as to the power supply unit 8. The electronic device component 7 comprises a processor as well as a non-volatile memory, in which one or more computer programs are stored which can be executed by the processor and provide the functions of the measuring device 1. These functions can comprise, on the one hand, the control of the measuring device 1, and, on the other hand, the processing of spectra detected by the spectrograph 6 and the determination of measured values from the spectra. For example, the electronic device component 7 can be designed to determine, from the spectra, concentrations of one or more determined analytes in the measuring medium or measurands dependent thereon. The spectra or values derived therefrom can be wirelessly transmitted from the electronic device component 7 to the operator unit 12 by means of the radio interface 11.

In the example shown here, the operator unit 12 is designed as a smartphone or a tablet computer. It comprises a radio interface, which is compatible with the radio interface 11 and configured to detect and process the data transmitted by the radio interface 11 of the electronic device component 7 and, vice versa, also transmit data, such as commands and/or parameter values, via radio to the radio interface 11 of the electronic device component 7. The electronic device component 7 can process and/or store the data received in this way. The operator unit 12 has at least one processor and one non-volatile memory, in which a computer program, for example, a mobile application (i.e., mobile app), is stored which provides functionalities for displaying the information received from the measuring device 1, such as the spectra and/or the measured values determined therefrom. Additional functionalities of the mobile application allow for a parameterization of the measuring device 1 by means of the operator unit 12.

Opposite the window 16, an ultrasound generator 19 is arranged on a wall of the flow-through cell 13. Said ultrasound generator can be put into operation from time to time to clean the window 16. This can be initiated by means of a separate operating element from the outside, or the ultrasound generator 19 can be connected to and controlled by the electronic device component 7 (not shown in FIG. 1).

The measuring device 1 shown in FIG. 1 is especially compact as a result of the accommodation of all components in a single housing 3 and can be put into operation easily by affixing it to a process container and parameterizing it by means of the portable operator unit 12. In this way, it can be installed in the same way and by means of the same processes as traditional measuring devices, regardless of the fact that the use of spectrometric measuring devices in some areas of process measuring technology is not yet very common and established, so that special training or the addition of special processes is not required.

Figure 2:
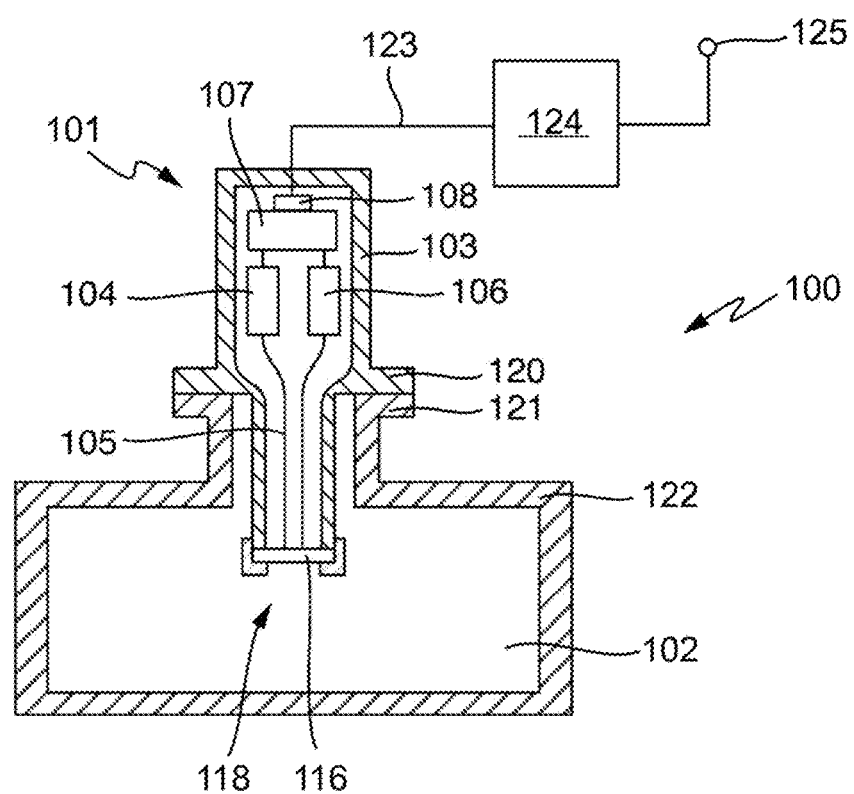
FIG. 2 shows a process measuring point with an embodiment of a spectrometric measuring device.

FIG. 2 schematically shows a process measuring point 100 with a spectrometric measuring device 101 for detecting Raman spectra according to a second exemplary embodiment. The measuring device 101 has a housing 103 and a process connection 120 firmly connected to the housing 103, which process connection is affixed to a connection 121, complementary to the process connection 120, of a process container 122. In the example shown here, the process container 122 is a reactor, which contains a process medium 102, in which a biotechnological process is performed.

In order to detect Raman spectra, the measuring device 101 has the same components as the measuring device 1 shown in FIG. 1, viz., a radiation source 104, a coupling and decoupling optical system 105 with wave guides and a window 116, a spectrograph 106, and an electronic device component 107, which can detect and process spectra registered by the spectrograph 106 and is also designed to control the measuring device 101. These parts of the measuring device 101 are designed completely analogously to the same parts of the measuring device 1 of the first exemplary embodiment and function in the same way.

The measuring device 101 is supplied with power via a switching power supply unit 108. Via the switching power supply unit 108, the measuring device 101 especially, also the electronic device component 107 is connected to a signal cable 123, which is in turn connected to an operator unit 124 comprising a measuring transducer. The measuring transducer can be connected via a fieldbus connection 125 to a fieldbus for communication, for example, in accordance with an industrial standard, such as Foundation Fieldbus, Profibus, Modbus, etc. Alternatively or additionally, the measuring transformer can also be designed to be Ethernet-enabled. Via the signal cable 123, which connects the measuring device 101 to the operator unit 124, power and data can preferably be transmitted simultaneously.

The housing 103 of the measuring device 101 has a portion protruding into the process container 122, which portion is closed on its process-side end by the window 116. Through the window 116, radiation can be decoupled into a measuring region 118, which is located in the process container and is filled by the measuring medium while the biotechnological process is carried out. In the measuring region 118, radiation scattered by molecules of the measuring medium can be coupled back into the device as measuring radiation through the window 116 and delivered to the spectrograph 106 in order to register spectra.

The operator unit 124 comprises at least one processor and one non-volatile memory, in which a computer program is stored which provides functionalities of the measuring transducer. These functionalities comprise the reception of spectra detected and possibly processed further by the electronic device component 107 and/or of data determined from the spectra by the electronic device component 107, such as measured values from the electronic device component 107. The operator unit 124 can process the spectra or data received and derive additional values therefrom. The measuring transducer can, especially, output the received spectra and/or data in the form of a signal to the fieldbus interface 125 according to an industrial standard, which signal can be processed by a higher-level unit connected to the operator unit 124 via the fieldbus.

The operator unit 124 can have a display, e.g., in the form of a display unit, on which the spectra and values derived therefrom can be displayed. The operator unit 124 can further have an input unit, such as a keyboard, switch, or touchscreen, via which a user can enter commands or parameters. In this way, the operator unit 124 can serve to parameterize the measuring device 101.

In an advantageous embodiment, the housing 103 can be designed to be explosion-proof, e.g., in accordance with the protection class Ex-d (pressure-tight encapsulation).

Figure 3:
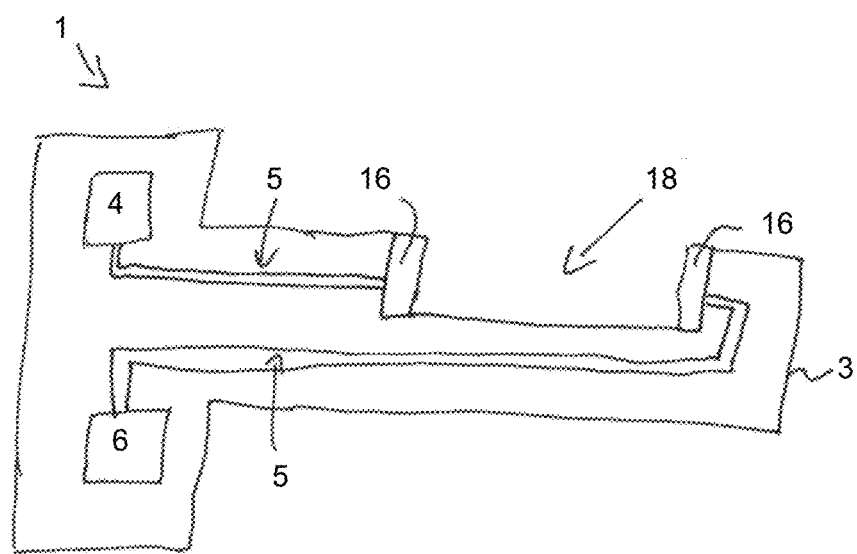
FIG. 3 shows an alternative embodiment of a spectrometric measuring device.
Figure 5:
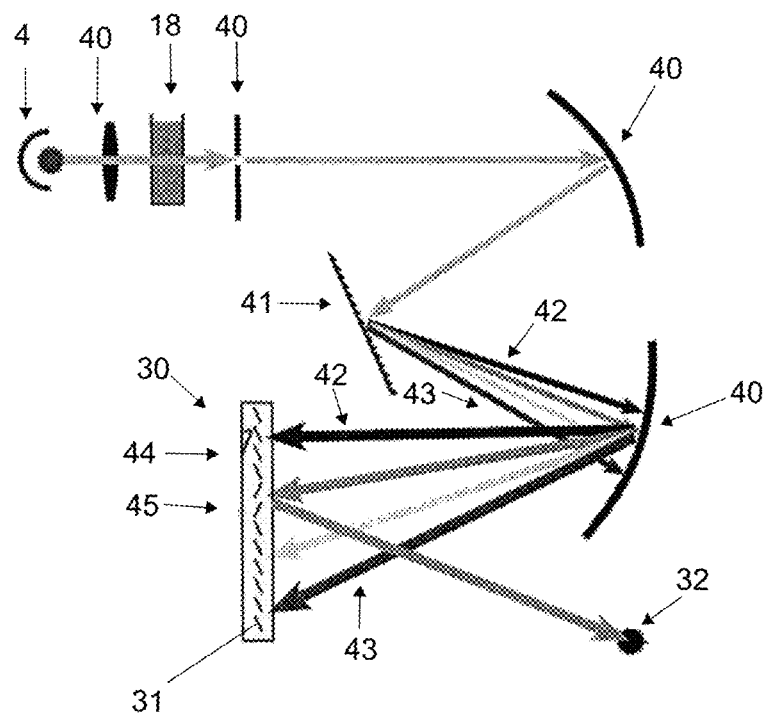
FIG. 5 shows a further embodiment of a spectrometric measuring device.

FIG. 3 and FIG. 5 show additional embodiments of the claimed spectrometric measuring device. Without restricting the scope of protection, the same reference symbols as in FIG. 1 shall be used below for the same features, e.g., the spectrometric measuring device has the reference symbol "1."

FIG. 3 shows another embodiment of the measuring device 1. In this case, only the certain components are shown, and only the differences from the previous exemplary embodiments are discussed. The arrangement comprises a radiation source 4, which emits radiation toward the measuring medium by means of a coupling and decoupling optical system 5. The radiation source 4 is in this case designed as an infrared light source. The coupling and decoupling optical system 5 can also comprise a wave guide. The coupling and decoupling optical system 5 comprises an optical window 16, through which the radiation arrives in the measuring region 18. The measuring medium is located in the measuring region 18, or flows around or through the measuring region 18. Alternatively, the measuring region 18 comprises a cuvette, which is then meaningfully used there. Where applicable, an optical window made of glass can also be omitted, if the wall of the housing 3 is made of an appropriate material which is transparent to the radiation emitted by the radiation source 4. After the radiation passes through the measuring medium, it arrives as measuring radiation back in the housing 3 through an optical window 16. There, it is guided to the spectrograph 6 by means of a coupling and decoupling optical system 5. On the receiver side, a wave guide can also guide the measuring radiation from the receiver-side optical window 16 to the spectrograph 6. All of the components described above are located in the housing 3.

Figure 4:
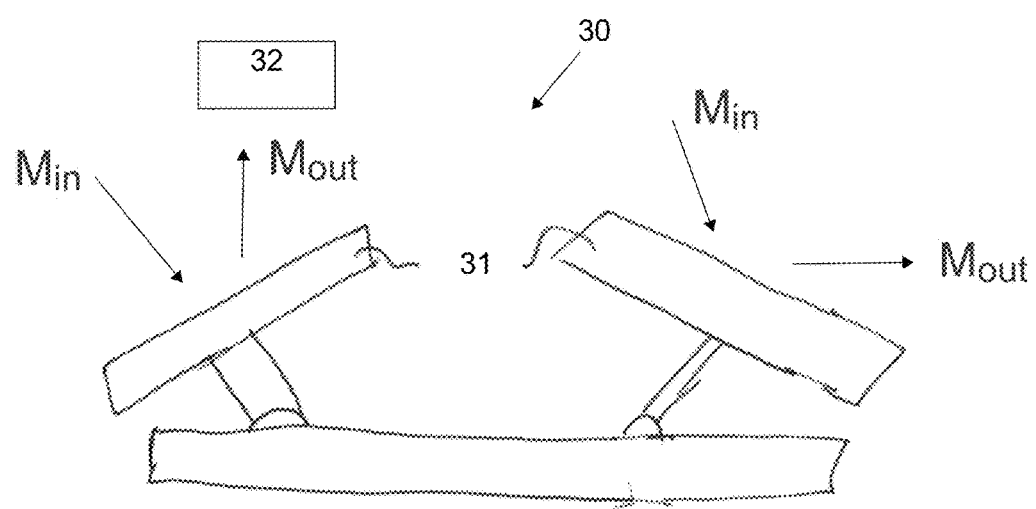
FIG. 4 shows a schematic diagram of a mirror device.

The spectrograph 6 comprises a mirror device 30, which deflects incoming measuring radiation $M_{in}$ toward the detector 32. In this case, the mirror device 30 comprises several individual mirrors 31, which can be tilted at least between a first position and second position. The mirror device 30 is designed as a digital mirror device (DMD). This is shown in FIG. 4, where the left mirror 31 is in a first position, and the right mirror 31 is shown in a second position. In the first position, the mirror 31 guides the measuring radiation $M_{in}$ toward the detector 32 as reflected measuring radiation $M_{out}$, while the radiation incidence upon the second position does not strike the detector. The individual mirrors 31 can, for example, be turned by ±12°. In one embodiment, about 1 million of these mirrors 31 are located on one chip. A resolution of, for example, 912×1140 mirrors results. The distance between the individual mirrors can be a few micrometers, e.g., 7.6 µm. A very fast response time and movement time of the mirrors is preferred, for example, 5 µs.

FIG. 5 shows an embodiment in which the measuring device 1 with a mirror device 30 is explained in more detail. After the radiation is emitted by the light source 4 and passes through the measuring medium in the measuring region 18, various optical elements 40 may possibly be required, which are not explained in more detail here. Examples thereof are focusing lenses or collimation lenses or focusing mirrors. The exemplary embodiment comprises an optical element 41, which splits the measuring radiation into its spectral portions thus, generally, a dispersion element. Examples thereof are a lattice, for example, a diffraction lattice, corresponding lenses, or a prism. In the example, downstream of the lattice 41, radiation of a shorter wavelength 42 is located in the upper region, and light of a longer wavelength 43 is located in the lower region of the figure.

The radiation now strikes the mirror device 30. As a result of the spectral splitting of the measuring radiation by means of the dispersion element 41, light now strikes the mirror device 30 at various locations. Depending upon which wavelength is to be detected, only the corresponding mirrors 31 are turned over, i.e., the mirrors 31 are turned over between the first and second positions according to the spectral portion of the measuring radiation. A first mirror 44 turns over if light of the shorter wavelength 42 strikes it and guides the light accordingly toward the detector 32. A second mirror 45 turns over if light of the longer wavelength 43 strikes it and guides the light accordingly toward the detector 32. All mirrors 31 can be turned over independently of each other. Naturally, several mirrors 31 can also be turned over at the same time, especially if the beam striking the mirror device 30 is larger than a single mirror 31. The detector 32 is designed as a single-point detector, i.e., a diode array or matrix is not required.

Figure 6:
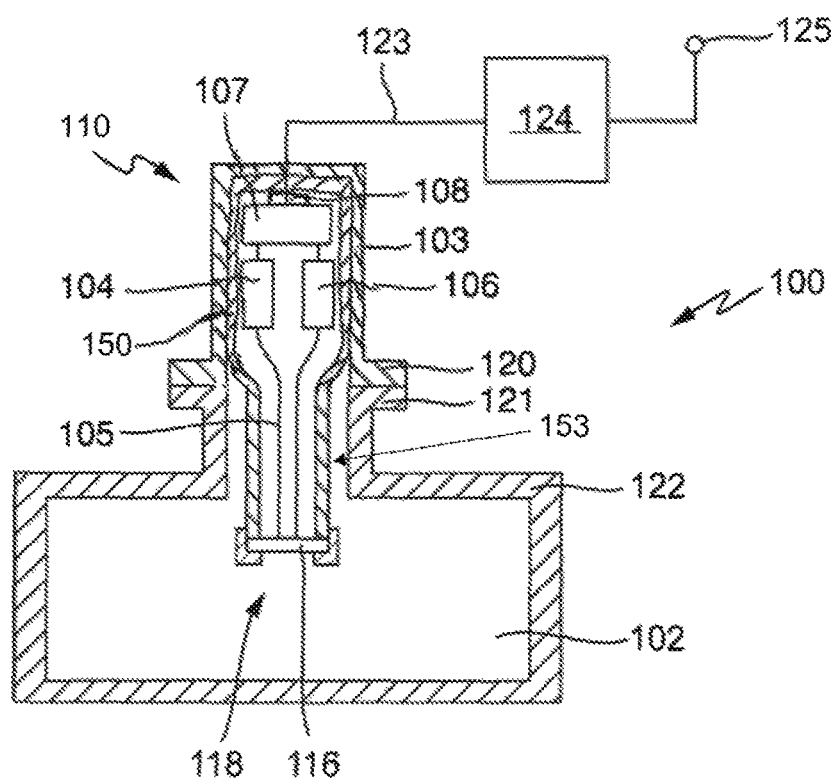
FIG. 6 shows a process measuring point with a further embodiment of a spectrometric measuring device.

A variety of additional embodiments of the measuring device according to the present disclosure beyond the exemplary embodiments described in detail here is conceivable. For example, FIG. 6 shows a spectrometric measuring device 110 connected to the process container 122 via an immersion changeover device 150 structured to move at least a portion 153 of the housing 103 adjacent the process container, which allows for regular cleaning, calibrating, and/or adjusting of the measuring device, without having to disconnect it from the process container.

The invention claimed is:

1. A spectrometric measuring device for a process measuring point, comprising:
   a housing;
   a radiation source disposed in the housing;
   a coupling and decoupling optical system structured to decouple radiation of the radiation source from the housing and direct the radiation into a measuring medium in a measuring region external to the housing, and to couple measuring radiation from the measuring region into the housing;
   a spectrograph disposed in the housing and aligned in relation to the coupling and decoupling optical system such that the measuring radiation coupled into the housing from the measuring region is detected by the spectrograph, wherein the spectrograph is configured to disperse the measuring radiation into a spectrum and to register the spectrum using a detector;
   an electronic device disposed in the housing and connected to the detector, the electronic device configured to detect and process the registered spectrum to determine, based upon the spectrum, a measurand correlated to the concentration of at least one analyte in the measuring medium; and a process connection connected to the housing, the connection structured to enable connecting the housing to a process container containing the measuring medium, wherein the measuring region is located within a volume area of the process container, said volume area containing the measuring medium, wherein the coupling and decoupling optical system includes a first wave guide that transmits radiation from the radiation source to the measuring medium and/or a second wave guide that transmits the measuring radiation from the measuring medium to the spectrograph, and wherein the connection includes a process connection structured to affix to a complementary connection of the process container, wherein the process container is a pipe carrying the measuring medium or a reaction container containing the measuring medium.

2. The spectrometric measuring device of claim 1, the spectrometric measuring device further comprising a power supply unit disposed in the housing and configured to supply power to the radiation source and the electronic device.

3. The spectrometric measuring device of claim 1, wherein the connection includes a flow-through cell or a spool piece having flanges on two opposite ends and structured to affix to the process container.

4. The spectrometric measuring device of claim 1, wherein the electronic device includes a microprocessor and a non-volatile memory, in which a computer program is stored that provides functionalities of the spectrometric measuring device and can be executed by the microprocessor, wherein the computer program serves to control the spectrometric measuring device, including the radiation source, controllable parts of the coupling and decoupling optical system, the detector and/or the power supply unit, and to register and process the spectrum.

5. The spectrometric measuring device of claim 4, wherein the spectrograph and the electronic device are configured to register and process a Raman spectrum formed by Stokes scattering and/or anti-Stokes scattering.

6. The spectrometric measuring device of claim 1, wherein the radiation source includes a substantially monochromatic radiation source, and wherein the measuring radiation coupled into the housing from the measuring region is generated by Raman scattering of the radiation of the radiation source directed into the measuring region.

7. The spectrometric measuring device of claim 6, wherein the spectrograph includes an optical filter structured to remove a portion of the measuring radiation generated by Rayleigh scattering.

8. The spectrometric measuring device of claim 1, wherein the coupling and decoupling optical system includes a window arranged in a wall of the housing and transparent to the radiation of the radiation source and to the measuring radiation.

9. The spectrometric measuring device of claim 8, the spectrometric measuring device further comprising an ultrasound source arranged outside of the housing at or near the window, the ultrasound source configured to clean the window.

10. The spectrometric measuring device of claim 1, wherein the housing is explosion-proof according to requirements for pressure-tight encapsulation as defined by a protection class Ex-d industry standard.

11. The spectrometric measuring device of claim 1, wherein the electronic device has an interface for wireless or wired communication with a control unit arranged outside the housing.

12. The spectrometric measuring device of claim 1, wherein the electronic device has a communication interface configured to send signals wirelessly to an operator unit and to receive signals wirelessly from the operator unit.

13. The spectrometric measuring device of claim 1, wherein the electronic device and/or the control unit and/or the operator unit have a processor and a non-volatile memory, in which a computer program is stored that can be executed by the processor, the computer program configured to determine from the registered spectrum a concentration of the analyte in the measuring medium or a value derived therefrom.

14. The spectrometric measuring device of claim 13, wherein the analyte is glucose.

15. The spectrometric measuring device of claim 1, wherein the radiation source emits radiation of a wavelength in the infrared range.

16. The spectrometric measuring device of claim 1, the spectrometric measuring device further comprising a mirror device that deflects incoming measuring radiation toward the detector.

17. The spectrometric measuring device of claim 16, wherein the mirror device includes a first mirror and a second mirror structured to be tilted independently of each other at least between a first position and a second position, wherein when in the first position the first mirror and the second mirror deflect the measuring radiation toward the detector.

18. The spectrometric measuring device of claim 17, the spectrometric measuring device further comprising a dispersion element structured to split the measuring radiation into measuring radiation of at least a first wavelength and a second wavelength, wherein the first mirror deflects the measuring radiation of the first wavelength toward the detector, and the second mirror deflects the measuring radiation of the second wavelength toward the detector.

19. The spectrometric measuring device of claim 1, wherein the detector is a single-point detector.

20. A process measuring point comprising:
at least one spectrometric measuring device comprising:
a housing;
a radiation source disposed in the housing;
a coupling and decoupling optical system structured to decouple radiation of the radiation source from the housing and direct the radiation into a measuring medium in a measuring region external to the housing, and to couple measuring radiation from the measuring region into the housing;
a spectrograph disposed in the housing and aligned in relation to the coupling and decoupling optical system such that the measuring radiation coupled into the housing from the measuring region is detected by the spectrograph, wherein the spectrograph is configured to disperse the measuring radiation into a spectrum and to register the spectrum using a detector, and wherein the coupling and decoupling optical system includes a first wave guide that transmits radiation from the radiation source to the measuring medium and/or a second wave guide that transmits the measuring radiation from the measuring medium to the spectrograph;

an electronic device disposed in the housing and connected to the detector, the electronic device configured to detect and process the registered spectrum to determine, based upon the spectrum, a measurand correlated to the concentration of at least one analyte in the measuring medium; and a process connection connected to the housing, the connection structured to enable connecting the housing to a process container containing the measuring medium, wherein the measuring region is located within a volume area of the process container, said volume area containing the measuring medium; and a process container connected to the housing of the spectrometric measuring device via the connection, wherein the connection includes a process connection structured to affix to a complementary connection of the process container, wherein the process container is a pipe carrying the measuring medium or a reaction container containing the measuring medium.

21. The process measuring point of claim 20, wherein the connection includes an immersion changeover device integrated into a wall of the process container, the immersion changeover device structured to move at least a portion of the housing adjacent the process container, which includes a window embodied to couple and decouple radiation into the measuring region of the process container, between a service position retracted into a service chamber of the immersion changeover device and a measuring position extended into the process container.

22. The process measuring point of claim 20, the process measuring point further comprising a control unit disposed outside the housing and connected to the electronic device for communication and/or an operator unit disposed outside the housing and connected to the electronic device for wireless or wired communication.

23. A spectrometric measuring device for a process measuring point, comprising:
   a housing;
   a radiation source disposed in the housing;
   a coupling and decoupling optical system structured to decouple radiation of the radiation source from the housing and direct the radiation into a measuring medium in a measuring region external to the housing, and to couple measuring radiation from the measuring region into the housing;
   a spectrograph disposed in the housing and aligned in relation to the coupling and decoupling optical system such that the measuring radiation coupled into the housing from the measuring region is detected by the spectrograph, wherein the spectrograph is configured to disperse the measuring radiation into a spectrum and to register the spectrum using a detector;
   an electronic device disposed in the housing and connected to the detector, the electronic device configured to detect and process the registered spectrum to determine, based upon the spectrum, a measurand correlated to the concentration of at least one analyte in the measuring medium; and
   a connection connected to the housing, the connection structured to enable connecting the housing to a process container containing the measuring medium, wherein the measuring region is located within a volume area of the process container, said volume area containing the measuring medium, and
   wherein the connection includes an immersion changeover device integrated into a wall of the process container, the immersion changeover device structured to move at least a portion of the housing adjacent the process container, which includes a window embodied to couple and decouple radiation into the measuring region of the process container, between a service position retracted into a service chamber of the immersion changeover device and a measuring position extended into the process container.

24. The spectrometric measuring device of claim 23, wherein the immersion changeover device is configured to move from the service position to the measuring position such that the immersion changeover device cannot be moved back to the service position.

* * * * *